(12) United States Patent
Johnson et al.

(10) Patent No.: US 6,559,101 B2
(45) Date of Patent: May 6, 2003

(54) N-(5,7-DIMETHOXY [1, 2, 4] TRIAZOLO [1, 5-A] PYRIMIDIN-2-YL) ARYLSULFONAMIDE COMPOUNDS AND THEIR USE AS HERBICIDES

(75) Inventors: Timothy Calvin Johnson, Indianapolis, IN (US); John Cord VanHeertum, Concord, CA (US); David George Ouse, Indianapolis, IN (US); Kim Eric Arndt, Carmel, IN (US); Mark Andrew Pobanz, Indianapolis, IN (US); David Keith Walker, Indianapolis, IN (US)

(73) Assignee: Dow AgroSciences LLC, Indianapolis, IN (US)

(*) Notice: Subject to any disclaimer, the term of this patent is extended or adjusted under 35 U.S.C. 154(b) by 0 days.

(21) Appl. No.: 10/000,935

(22) Filed: Nov. 2, 2001

(65) Prior Publication Data

US 2002/0111361 A1 Aug. 15, 2002

Related U.S. Application Data

(60) Provisional application No. 60/245,836, filed on Nov. 3, 2000.

(51) Int. Cl.$^7$ .................... C07D 487/04; A01N 43/90
(52) U.S. Cl. .................... 504/241; 544/256
(58) Field of Search .................... 544/256; 504/241

(56) References Cited

U.S. PATENT DOCUMENTS

| 4,638,075 A | 1/1987 | Kleschick et al. | 558/5 |
| 4,685,958 A | 8/1987 | Pearson et al. | 71/93 |
| 4,822,404 A | 4/1989 | Kleschick | 71/92 |
| 5,163,995 A | 11/1992 | Van Heertum et al. | 71/92 |
| 5,571,775 A | 11/1996 | Van Heertum et al. | 504/246 |
| 5,858,924 A | 1/1999 | Johnson et al. | 504/241 |

FOREIGN PATENT DOCUMENTS

| DE | 3539386 A1 | 11/1985 |

*Primary Examiner*—Venkataraman Balasubramanian
(74) *Attorney, Agent, or Firm*—Craig E. Mixan

(57) ABSTRACT

N-(5,7-dimethoxy[1,2,4]triazolo[1,5-a]pyrimidin-2-yl) arylsulfonamide compounds were prepared from 2-amino-5,7-dimethoxy[1,2,4]triazolopyrimidine and appropriately substituted benzenesulfonyl chloride and pyridinesulfonyl chloride compounds. The compounds were found to be useful as herbicides.

31 Claims, No Drawings

N-(5,7-DIMETHOXY [1, 2, 4] TRIAZOLO [1,5-A] PYRIMIDIN-2-YL) ARYLSULFONAMIDE COMPOUNDS AND THEIR USE AS HERBICIDES

CROSS-REFERENCE TO RELATED APPLICATIONS

This application claims priority from U.S. provisional application Ser. No. 60/245,836, which was filed on Nov. 3, 2000.

BACKGROUND OF THE INVENTION

The present invention relates to substituted benzenesulfonamide and pyridinesulfonamide compounds, to herbicidal compositions containing the compounds, and to the utility of the compounds for the control of unwanted vegetation.

The control of unwanted vegetation by means of chemical agents, i.e., herbicides, is an important aspect of modern agriculture and land management. While many chemicals that are useful for the control of unwanted vegetation are known, new compounds that are more effective generally, are more effective for specific plant species, are less damaging to desirable vegetation, are safer to man or the environment, are less expensive to use, or have other advantageous attributes are desirable.

Many substituted benzenesulfonamide compounds are known and certain of them are known to possess herbicidal activity. For example, certain N-([1,2,4]triazolo[1,5-a]pyrimidin-2-yl)benzenesulfonamide compounds and their herbicidal utility were disclosed in U.S. Pat. No. 4,638,075 and certain N-([1,2,4]triazolo[1,3,5]triazin-2-yl) benzenesulfonamide compounds were disclosed in U.S. Pat. No. 4,685,958. In addition, certain N-([1,2,4]triazolo[1,5-c]pyrimidin-2-yl) benzenesulfonamide, N-([1,2,4]triazolo[1,5-c]pyrimidin-2-yl)pyridinesulfonamide, N-([1,2,4]triazolo[1,5-a]pyridin-2-yl)benzenesulfonamide, and N-([1,2,4]triazolo[1,5-a]pyridin-2-yl)pyridinesulfonamide compounds were disclosed in U.S. Pat. No. 5,858,924. Certain N-phenyl arylsulfonamide compounds are also known and are known to possess herbicidal activity. For example, certain N-(substituted phenyl)[1,2,4]triazolo[1,5-c]pyrimidin-2-sulfonamide compounds were disclosed in U.S. Pat. No. 5,163,995 and certain N-(substituted phenyl)[1,2,4]triazolo[1,5-a]pyridin-2-sulfonamide compounds were disclosed in U.S. Pat. No. 5,571,775.

SUMMARY OF THE INVENTION

It has now been found that a class of novel N-(5,7-dimethoxy[1,2,4]triazolo[1,5-a]pyrimidin-2-yl) arylsulfonamide compounds are potent herbicides for the control of unwanted vegetation by either preemergence or postemergence application. The invention includes N-(5,7-dimethoxy [1,2,4]triazolo[1,5-a]pyrimidin-2-yl)benzenesulfonamide and pyridinesulfonamide compounds of Formula I:

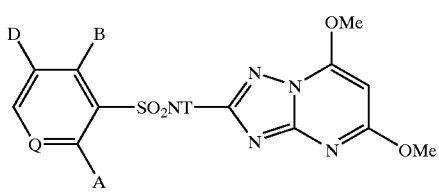

wherein

Q represents N or C—H;

A and B independently represent H, halo, R, OR' or $CO_2R''$ with the proviso that A and B are not both H;

D represents H, halo, or R;

T represents H, $SO_2R''$, $C(O)R''$, $C(O)OR''$, $C(O)NR''_2$, or $CH_2CH_2C(O)OR''$;

R represents $C_1-C_3$ alkyl each optionally possessing up to the maximum possible number of fluoro substituents;

R' represents $C_1-C_4$ alkyl, $C_3-C_4$ alkenyl, or $C_3-C_4$ alkynyl each optionally possessing up to the maximum possible number of fluoro substituents; and R" represents H or $C_1-C_4$ alkyl and, when T represents H, the agriculturally acceptable salts thereof.

Compounds wherein Q represents each of N and C—H are among the preferred compounds of the invention. T most preferably represents H. Some of the preferred compounds further possess an ortho methoxy substituent (A or B) in combination with a variety of substituents in the other ortho position (A or B) and hydrogen in the meta position (D); an ortho methoxy substituent (A) in combination with hydrogen or a meta methyl or chloro substituent (D) and no substituent in the other ortho position (B); or an ortho trifluoromethyl substituent (B) in combination with a variety of substituents in the other ortho position (A) and hydrogen in the meta position (D).

The invention further includes compositions containing herbicidal amounts of compounds of Formula I in combination with one or more agriculturally acceptable adjuvants or carriers and the use of the compounds of Formula I as herbicides. The use of suitable compounds of the invention to achieve total vegetation control is generally preferred. Both grassy and broadleaf weeds can be controlled. Postemergence application of the compounds to undesirable vegetation is generally preferred.

DETAILED DESCRIPTION OF THE INVENTION

The N-(5,7-dimethoxy[1,2,4]triazolo[1,5-a]pyrimidin-2-yl)arylsulfonamide compounds of the invention can generally be described as substituted benzenesulfonamide and pyridine-3-sulfonamide compounds possessing, on the amide nitrogen atom, a 5,7-dimethoxy[1,2,4]triazolo[1,5-a]pyrimidin-2-yl moiety.

The herbicidal compounds of the invention are N-(5,7-dimethoxy[1,2,4]triazolo[1,5-a]pyrimidin-2-yl) benzenesulfonamide and pyridinesulfonamide compounds of generic Formula I:

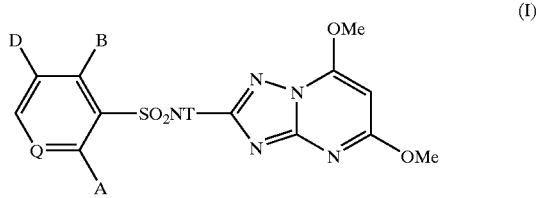

Compounds in which Q represents N are pyridinesulfonamide compounds, those in which Q represents C—H are benzenesulfonamide compounds. The compounds are further characterized by possessing at least one substituent (A or B) adjacent to the sulfonamide on the benzene or pyridine ring.

Compounds of the invention include compounds of Formula I wherein A and B independently represent H, halo, R, OR' or $CO_2R''$ provided that A and B are not both H. A is preferably R, OR' or $CO_2R''$, and most preferably OR'.

For compounds of the present invention, R represents $C_1-C_3$ alkyl, each optionally possessing up to the maximum possible number of fluoro substituents. R is preferably $CH_3$, $CH_2CH_3$, $CF_3$ and $CF_2CF_3$.

For compounds of the present invention, R' can be $C_1$–$C_4$ alkyl, $C_3$–$C_4$ alkenyl, or $C_3$–$C_4$ alkynyl each optionally possessing up to the maximum possible number of fluoro substituents. For OR', R' is preferably $C_1$–$C_4$ alkyl optionally possessing up to the maximum possible number of fluoro substituents. Most preferably, R' is $CH_3$, $CH_2CH_3$, $CH(CH_3)_2$, $CH_2CH_2F$, $CH_2CHF_2$ and $CH_2CF_3$.

For compounds of the present invention, R" can be H or $C_1$–$C_4$ alkyl. R" is preferably $CH_3$ or $CH_2CH_3$.

The compounds of Formula I include those wherein T represents hydrogen, an alkylsulfonyl group ($SO_2R$"), an acyl group (C(O)R"), an alkoxycarbonyl group (C(O)OR"), an aminocarbonyl group (C(O)NR"$_2$), or a 2-(alkoxycarbonyl)ethyl group ($CH_2CH_2C(O)OR$"), wherein R" represents $C_1$–$C_4$ alkyl. Such compounds wherein T represents hydrogen are preferred. When T represents hydrogen, the invention further includes the agriculturally acceptable salts of compounds of the Formula I.

Compounds of Formula I which possess each possible combination of preferred, more preferred, most preferred, desirable, and special interest substituents are, further, considered to be important embodiments of the invention.

The terms alkyl, alkenyl, and alkynyl (including when modified as in haloalkyl and alkoxy) as used herein include straight chain, branched chain, and cyclic groups. Thus, typical alkyl groups are methyl, ethyl, 1-methylethyl, propyl, 1,1-dimethylethyl, and cyclopropyl. Methyl and ethyl are often preferred. Alkyl groups are sometimes referred to herein as normal (n), iso (i), secondary (s) or tertiary (t). Typical alkyl with up to the maximum possible number of fluoro substituents include trifluoromethyl, monofluoromethyl, 2,2,2-trifluoroethyl, 2,3-difluoropropyl, and the like; trifluoromethyl is often preferred. The term halogen includes fluorine, chlorine, bromine, and iodine.

The term "agriculturally acceptable salts" is employed herein to denote compounds wherein the acidic sulfonamide proton of the compound of Formula I is replaced by a cation which itself is neither herbicidal to crop plants being treated nor significantly deleterious to the applicator, the environment, or the ultimate user of any crop being treated. Suitable cations include, for example, those derived from alkali or alkaline earth metals and those derived from ammonia and amines. Preferred cations include sodium, potassium, magnesium, and aminium cations of the formula:

$R^2R^3R^4NH^+$ wherein $R^2$, $R^3$, and $R^4$ each, independently represents hydrogen or ($C_1$–$C_{12}$)alkyl, ($C_3$–$C_{12}$)cycloalkyl, or ($C_3$–$C_{12}$)alkenyl, each of which is optionally substituted by one or more hydroxy, ($C_1$–$C_8$)alkoxy, ($C_1$–$C_8$)alkylthio or phenyl groups; provided that $R^2$, $R^3$, and $R^4$ are sterically compatible. Additionally, any two of $R^2$, $R^3$, and $R^4$ together may represent an aliphatic difunctional moiety containing 1 to 12 carbon atoms and up to two oxygen or sulfur atoms. Salts of the compounds of Formula I can be prepared by treatment of compounds of Formula I wherein V represents hydrogen with a metal hydroxide, such as sodium hydroxide, potassium hydroxide, or magnesium hydroxide, or an amine, such as ammonia, trimethylamine, hydroxyethylamine, bisallylamine, 2-butoxyethylamine, morpholine, cyclododecylamine, or benzylamine.

The compounds of Table 1 are examples of the compounds of the invention. Some of the specifically preferred compounds of Formula I, which vary depending on the weed species to be controlled, the crop present (if any), and other factors, include the following compounds of Table 1: N-(5,7-dimethoxy[1,2,4]triazolo[1,5-a]pyrimidin-2-yl)-2,6-dichlorobenzenesulfonamide, N-(5,7-dimethoxy[1,2,4]triazolo[1,5-a]pyrimidin-2-yl)-2-(2-fluoroethoxy)-6-(trifluoromethyl)benzenesulfonamide, N-(5,7-dimethoxy[1,2,4]triazolo[1,5-a]-pyrimidin-2-yl)-2-ethoxy-6-(trifluoromethyl)benzenesulfonamide and N-(5,7-dimethoxy[1,2,4]triazolo[1,5-a]pyrimidin-2-yl)-2-methoxy-4-(trifluoromethyl)-3-pyridinesulfonamide.

TABLE 1

SULFONAMIDE COMPOUNDS

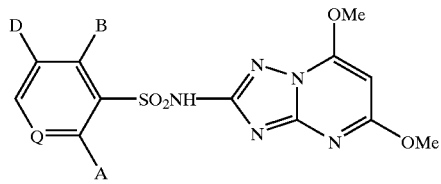

| Cpd. No. | Q | A | B | D | Form | Melting Point, °C. | Elem. Anal. Calc./Found | | |
|---|---|---|---|---|---|---|---|---|---|
| | | | | | | | % C | % H | % N |
| 1 | C—H | Cl | Cl | H | White powder | 211–213 | 38.6 | 2.74 | 17.3 |
| | | | | | | | 38.1 | 2.68 | 16.8 |
| 2 | C—H | $OCH_3$ | $OCH_3$ | H | tan powder | 190–193 | 45.6 | 4.33 | 17.7 |
| | | | | | | | 40.4 | 4.02 | 14.5 |
| 3 | C—H | $CF_3$ | $OCH_2CH_2F$ | H | tan powder | 195–197 | 41.3 | 3.25 | 15.1 |
| | | | | | | | 40.8 | 3.13 | 14.5 |
| 4 | C—H | $CF_3$ | $OCH_3$ | H | yellow powder | 216–218 | 41.6 | 3.03 | 16.1 |
| | | | | | | | 38.7 | 3.05 | 14.3 |
| 5 | C—H | $OCH_3$ | H | Cl | white powder | 210–213 | 42.1 | 3.53 | 17.5 |
| | | | | | | | 42.0 | 3.51 | 17.3 |
| 6 | C—H | $OCH_3$ | H | $CH_3$ | white powder | 218–220 | 47.5 | 4.52 | 18.5 |
| | | | | | | | 47.3 | 4.48 | 17.3 |
| 7 | C—H | $CO_2CH_3$ | $OCH_3$ | H | white powder | 198–201 | 45.4 | 4.05 | 16.5 |
| | | | | | | | 45.4 | 4.15 | 15.9 |

TABLE 1-continued

SULFONAMIDE COMPOUNDS

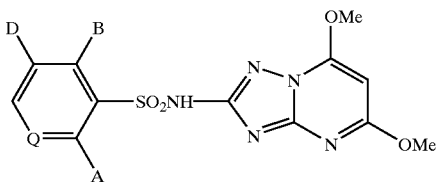

| Cpd. No. | Q | A | B | D | Form | Melting Point, °C. | % C | % H | % N |
|---|---|---|---|---|---|---|---|---|---|
| 8 | C—H | $CF_3$ | $OCH_2CHF_2$ | H | white powder | 203–204 | 39.8 / 40.0 | 2.92 / 2.82 | 14.5 / 14.4 |
| 9 | C—H | $OCH_3$ | H | $CH_2CH_3$ | white powder | 214–216 | 48.9 / 49.1 | 4.87 / 4.89 | 17.8 / 17.2 |
| 10 | C—H | $OCH_2CH_3$ | H | $CH_3$ | | 204–206 | 48.9 / 48.6 | 4.87 / 5.01 | 17.8 / 16.4 |
| 11 | C—H | $OCH(CH_3)_2$ | $CF_3$ | H | white powder | 203–204 | 39.8 / 40.0 | 2.92 / 2.82 | 14.5 / 14.4 |
| 12 | C—H | $CF_3$ | $OCH_2CF_3$ | H | | 155–156 | 38.3 / 36.6 | 2.60 / 2.70 | 13.9 / 10.9 |
| 13 | C—H | $OCH_2CH_2F$ | H | Cl | salmon powder | 198–200 | 41.7 / 40.7 | 3.50 / 3.48 | 16.2 / 14.6 |
| 14 | C—H | $CF_3$ | $OCH_2CH_3$ | H | tan powder | 207–209 | 42.9 / 42.9 | 3.60 / 3.61 | 15.7 / 14.0 |
| 15 | N | $OCH_3$ | CF3 | H | tan powder | 194–195 | 38.7 / 38.4 | 3.02 / 2.92 | 19.4 / 19.0 |
| 16 | N | F | $CF_3$ | H | white powder | 206–207 | 37.0 / 37.3 | 2.39 / 2.34 | 19.9 / 20.1 |
| 17 | N | $OCH_3$ | I | H | white powder | 187–188 | 31.7 / 31.9 | 2.66 / 2.50 | 17.1 / 16.8 |
| 18 | N | $OCH_3$ | $CF_2CF_3$ | H | white powder | 204–205 | 37.2 / 36.9 | 2.71 / 2.90 | 17.6 / 17.0 |
| 19 | N | $OCH_2CH_3$ | $CF_3$ | H | | 195–196 | 40.2 / 40.5 | 3.37 / 3.68 | 18.7 / 18.0 |

The compounds of Formula I wherein T represents hydrogen can be prepared by the reaction of 2-amino-5,7-dimethoxy[1,2,4]triazolopyrimidine of Formula II:

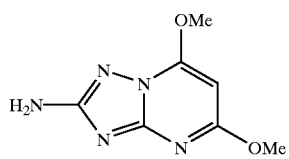

(II)

with a arylsulfonyl chloride compound of Formula III:

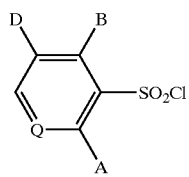

(III)

wherein A, B, D and Q are as defined for compounds of Formula I. The reaction can be carried out by combining approximately equal molar amounts of the two compounds in a polar, aprotic solvent, such as acetonitrile, and adding pyridine and a catalytic amount (5 to 25 molar percent of the sulfonyl chloride compound) of dimethyl sulfoxide at room temperature. Additional sulfonyl chloride compound, pyridine, and dimethyl sulfoxide are added, if necessary, to complete the reaction. The reactions take from a few hours to several days to go to completion. Means to exclude moisture, such as a dry nitrogen blanket, are employed. The compounds of Formula I obtained, which are solids with low solubility in many common organic solvents and in water, can be recovered using conventional means.

N-(5,7-dimethoxy[1,2,4]triazolo[1,5-a]pyrimidin-2-yl) arylsulfonamide compounds of Formula I wherein T represents other than hydrogen can be prepared from the corresponding compounds of Formula I wherein T represents hydrogen by acylation under reaction conditions known in the art for related sulfonamide acylation reactions. Suitable acylating agents include alkanoyl chloride compounds, such as propionyl chloride or trifluoroacetyl chloride; chloroformate ester compounds, such as 2-methoxyethyl chloroformate; carbamoyl chloride compounds, such as N',N'-diallyl-carbamoyl chloride, and alkyl isocyanate compounds, such as 2-chloroethyl isocyanate.

The 2-amino-5,7-dimethoxy[1,2,4]triazolopyrimidine of Formula II can be prepared by the reaction of N-(4,6-dimethoxypyrimidin-2-yl)-N'-carboethoxythiourea of the formula

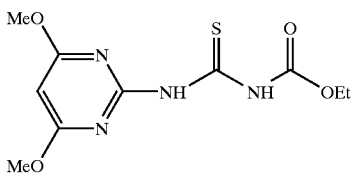

with hydroxylamine. The reaction is typically carried out in a solvent such as ethanol and requires heating for a few hours. The hydroxylamine is typically generated by neutralization of the hydrochloride with a hindered tertiary amine, such as diisopropylethylamine, or an alkali metal alkoxide, such as sodium ethoxide. The desired compound of Formula II can be recovered by conventional means, such as by removal of the volatile components of the reaction mixture by evaporation, and can be purified by conventional means, such as by extraction with water and/or other solvents in which they are sparingly soluble. The N-(4,6-dimethoxypyrimidin-2-yl)-N'-carboethoxythiourea starting material for this method can be obtained by treatment of 2-amino-4,6-dimethoxypyrimidine with ethoxycarbonyl isothiocyanate. The reaction is generally carried out in an inert organic solvent at ambient temperatures. The overall method is further described in U.S. Pat. No. 5,571,775.

The 2-amino-4,6-dimethoxypyrimidine starting material for the method described above is known in the art.

The substituted benzenesulfonyl chloride and pyridinesulfonyl chloride starting materials of Formula III can be prepared by the methods disclosed herein or by general or specific methods known in the art. Many such compounds, such as 2-methoxy-6-(trifluoromethyl) benzenesulfonyl chloride and 2-methoxy-4-(trifluoromethyl)-3-pyridinesulfonyl chloride, can be prepared by lithiation of the corresponding benzene or pyridine compound, e.g., 3-(trifluoromethyl)anisole or 2-methoxy-4-(trifluoromethyl) pyridine, with butyl lithium, reaction of the phenyl or pyridinyl lithium compound obtained with dipropyl disulfide, and then chloroxidation of the resulting propylthio compound. In each of these reaction steps, conditions generally known for such processes were used. Many propyl or benzylthiobenzenes and pyridines can also be prepared by alkylation of the corresponding thiophenol or 3-pyridinethiol compound using standard methods and subsequent chloroxidation. Phenyl and pyridinyl lithium compounds, such as that derived from 1,3-dimethoxybenzene can be converted directly to the corresponding desired sulfonyl chloride compounds by reaction with sulfur dioxide and sulfuryl chloride in the presence of N,N,N',N'-tetramethylethylenediamine. Other of the required sulfonyl chloride compounds can be prepared by diazotization of the corresponding aniline or 3-aminopyridine compounds in the presence of sulfur dioxide, copper chlorides, and concentrated aqueous hydrochloric acid. Benzenesulfonyl chloride compounds, such as 2-methoxy-5-methylbenzenesulfonyl chloride, can be prepared by direct chlorosulfonation of appropriate benzene compounds. 3-Alkylthiopyridine compounds having chloro substituents in the 2- and/or 4-positions can be converted to the corresponding compounds having other halo or alkoxy substituents by conventional nucleophilic displacement processes before chloroxidation to produce other pyridine-3-sulfonyl chloride compounds. The preparation of many of the desired benzenesulfonyl chlorides and pyridinesulfonyl chlorides is described in U.S. Pat. No. 5,858,924.

While it is possible to utilize the N-(5,7-dimethoxy[1,2,4]triazolo[1,5-a]pyrimidin-2-yl)arylsulfonamide compounds of Formula I directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, N-methyl-2-pyrrolidinone, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is frequently desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions can also contain other compatible components, for example, other herbicides, herbicide safeners, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.001 to about 5 weight percent active ingredient and preferably contain about 0.01 to about 0.5 percent.

The present compositions can be applied to weeds or their locus by the use of conventional ground or aerial dusters, sprayers, and granule applicators, by addition to irrigation water, and by other conventional means known to those skilled in the art.

The compounds of Formula I have been found to be useful preemergence (including pre-plant) and post-emergence herbicides. Postemergence applications are generally preferred. The compounds are effective in the control of both broadleaf and grassy weeds. While each of the N-(5,7-dimethoxy[1,2,4]triazolo[1,5-a]pyrimidin-2-yl)arylsulfonamide compounds encompassed by Formula I is within the scope of the invention, the degree of herbicidal activity, crop selectivity, and spectrum of weed control obtained varies depending upon the substituents and other features present. The compounds can be employed at higher, non-selective rates of application to control essentially all of the vegetation in an area. In some cases, the compounds can also be employed at lower, selective rates of application for the control of undesirable vegetation in grass crops or in broadleaf crops. In such instances, the selectivity can often be improved by the use of safeners.

The term herbicide is used herein to mean an active ingredient that controls or adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation are meant to include germinant seeds, emerging seedlings and established vegetation.

Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the compounds of Formula I postemergence to relatively immature plants to achieve the maximum control of weeds.

Application rates of about 0.001 to about 1 kg/ha are generally employed in postemergence operations; for preemergence applications, rates of about 0.01 to about 2 kg/ha are generally employed. The higher rates designated generally give non-selective control of a broad variety of undesirable vegetation. The lower rates typically give selective control and, by judicious election of compounds, timing, and rates of application, can be employed in the locus of crops.

The compounds of the present invention (Formula I) are often applied in conjunction with one or more other herbicides to obtain control of a wider variety of undesirable vegetation. When used in conjunction with other herbicides, the presently claimed compounds can be formulated with the other herbicide or herbicides, tank mixed with the other herbicide or herbicides, or applied sequentially with the other herbicide or herbicides. Some of the herbicides that can be employed beneficially in combination with the compounds of the present invention include substituted triazolopyrimidinesulfonamide compounds, such as diclosulam, florasulam, cloransulam-methyl, and flumetsulam. Other herbicides such as acifluorfen, bentazon, chlorimuron, clomazone, lactofen, carfentrazone-methyl, fumiclorac, fluometuron, fomesafen, imazaquin, imazethapyr, linuron, metribuzin, fluazifop, haloxyfop, glyphosate, glufosinate, 2,4-D, acetochlor, metolachlor, sethoxydim, nicosulfuron, clopyralid, fluroxypyr, metsulfuron-methyl, amidosulfuron, tribenuron, and others can also be employed. It is generally preferred to use the compounds in conjunction with other herbicides that have a similar crop selectivity. It is further usually preferred to apply the herbicides at the same time, either as a combination formulation or as a tank mix.

The compounds of the present invention can generally be employed in combination with a wide variety of known herbicide safeners, such as cloquintocet, mefenpyr, furilazole, dichlormid, benoxacor, flurazole, fluxofenim, daimuron, dimepiperate, thiobencarb, and fenclorim, to enhance their selectivity. Herbicide safeners that act by modifying the metabolism of herbicides in plants by enhancing the activity of cytochrome P-450 oxidases are usually especially effective. This is often a preferred embodiment of the invention. The compounds can additionally be employed to control undesirable vegetation in many crops that have been made tolerant to or resistant to herbicides by genetic manipulation or by mutation and selection. For example, crops that have been made tolerant or resistant to herbicides in general or to herbicides that inhibit the enzyme acetolactate synthase in sensitive plants can be treated.

EXAMPLES

The following Examples are presented to illustrate the various aspects of this invention and should not be construed as limitations to the claims.

1. Preparation of Ethyl N-[N'-(4,6-dimethoxypyrimidin-2-yl) thiocarbamoyl]carbamate 2-Amino-4,6-dimethoxypyrimidine (5.0 g, 36 mmol) was dissolved in dry tetrahydrofuran (THF, 35 mL), ethoxycarbonylisothiocyanate (6.4 mL, 54 mmol) was added and the solution was allowed to stir at room temperature. After 24 hours, the solvent is removed in vacuo and the residue was mixed with ether to form a crystalline solid. The solids were removed by vacuum filtration and dried to afford the product as a tan solid (8.9 g, 87%). mp 196–197° C. $^1$H NMR (CDCl$_3$): $\delta$13.2 (bs, 1H); 8.8 (bs, 1H); 5.80 (s, 1H); 4.32–4.25 (q, 2H, J=7.2); 3.93 (s, 3H); 1.30 (t, 3H, J=7.2).

2. Preparation of 2-amino-5,7-dimethoxy[1,2,4]triazolo[1,5-a]pyrimidine

Ethyl N-[N'-(4,6-dimethoxypyrimidin-2-yl)-thiocarbamoyl]carbamate (0.50 g, 1.7 mmol) was mixed with ethanol (5 mL). To this mixture was added hydroxylamine hydrochloride (0.12 g, 1.7 mmol) and diisopropylethylamine (0.30 mL, 1.7 mmol). The resulting mixture was allowed to stir at room temperature. After 2.5 hours, additional diisopropylethylamine (0.30 mL, 1.7 mmol) was added to the mixture. After 48 hours the ethanol was removed in vacuo and the residue was partitioned between H$_2$O and Et$_2$O to give a powder. The powder was filtered and dried to afford the product as a tan powder (0.27 g, 82%). mp 215–220° C. $^1$H NMR (DMSO-d$_6$): $\delta$6.04 (s, 1H); 5.97 (bs, 2H); 4.04 (s, 3H).

3. Preparation of N-(5,7-dimethoxy[1,2,4]triazolo-[1,5-a]pyrimidin-2-yl)-2,6-dichlorobenzene-sulfonamide (Compound 1)

2-Amino-5,7-dimethoxy[1,2,4]triazolo[1,5-a]-pyrimidine (0.75 g, 3.8 mmol) and 2,6-dichlorobenzene-sulfonyl chloride (1.86 g, 7.6 mmol) were mixed in dry acetonitrile (15 mL). To this mixture was added dry pyridine (0.61 mL) and dry DMSO (54 μL, 0.7 mmol). The mixture was allowed to stir at room temperature. After 24 hours, the solvent was removed in vacuo, the residue was partitioned between $CH_2Cl_2$ (300 mL) and 2N HCl and the solids were collected by vacuum filtration to give a white solid A. The $CH_2Cl_2$ was dried ($MgSO_4$) and removed in vacuo to give a white solid B. Both HPLC and NMR indicated that solid A and B are product. The solids were combined to afford the product as a white powder (1.41 g, 92%). mp 211–213° C. Anal: Cacld for $C_{13}H_{11}Cl_2N_5O_4S$: C, 38.63; H, 2.74; N, 17.33; S, 7.93; found: C, 38.11; H, 2.68; N, 16.83; S, 7.77. $^1$H NMR (DMSO-$d_6$): δ 12.4 (bs, 1H); 7.64–7.54 (m, 3H); 6.26 (s, 1H); 4.07 (s, 3H); 3.88 (s, 3H).

The other compounds of Table 1 were prepared similarly.

4. Preparation of Herbicidal Compositions Wettable Powder

Barden clay (55.5 g), HiSil 233 silica (5.0 g), Polyfon H (sodium lignosulfonate; 7.0 g), Stepanol ME-Dry (sodium lauryl sulfate; 7.9 g), and Compound 1 (20.4 g) were added to a 1 quart glass Waring blender cup and thoroughly mixed at high speed. The blended mixture was passed (one time) thru a laboratory Trost mill with the opposing jets set between 75 and 80 psi (517–551 kPa). This produced a wettable powder of excellent wettability and suspension power. By diluting this wettable powder with water it is possible to obtain suspensions of suitable concentrations for controlling weeds.

Aqueous Suspension Concentrate

To prepare an aqueous suspension concentrate, deionized water (106 g), Kelzan S (xanthan gum; 0.3 g), Avicel CL-611 (carboxylmethyl cellulose; 0.4 g), and Proxel GXL (1,2-benzisothiazolin-3-one; 0.2 g) were added to a blender and mixed for 30 min. Then Compound 3 (44 g), Darvan #1 (naphthalene sulfonate; 2 g), Foamaster UDB (silicone fluid; 0.2 g), Pluronic P-105 (ethylene oxide/propylene oxide block copolymer; 20 g), phosphoric acid (0.02 g), and propylene glycol (16 g) were added to the same blender and mixed for 5 min. Once blended the contents were milled in an Eiger mill filled with 1–1.25 mm lead free glass beads (40 mL) at 5000 rpm for 30 min. External cooling on the Eiger mill grinding chamber was maintained at 15° C.

Oil-based Suspension Concentrate

To a 1 quart glass Waring blender cup was added Exxon's crop oil (145.4 g), Amsul DMAP 60 (dimethylaminopropane salt of dodecybenzene sulfonic acid; 4.0 g) and Attagel 50 (attapulsite clay; 4.0 g). The mixture was thoroughly blended at high speed to insure homogeneity. The Amsul DMAP was difficult to disperse, but eventually formed small homogeneous globules. Agrimul 70-A (ethoxylated bismethylene octylphenol; 4.0 g) and Emulsogen M (oleyl alcohol-ethylene oxide; 16.0 g) were added and thoroughly blended until the mixture was uniform in texture. Cloquintocet mexyl (5.4 g) was then blended into the mixture followed by Compound 15 (21.3 g). The final grinding stock dispersion milled in the Eiger mill using the conditions described above for the aqueous suspension concentrate.

5. Evaluation of Postemergence Herbicidal Activity

Seeds of the desired test plant species were planted in Grace-Sierra MetroMix® 306 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7–21 days in a greenhouse with an approximately 15 hr photoperiod which was maintained at about 23–29° C. during the day and 22–28° C. during the night. Nutrients and water were added on a regular basis and supplemental lighting was provided with overhead metal halide 1000 Watt lamps as necessary. The plants were employed for testing when they reached the first or second true leaf stage.

A weighed amount of each test compound, determined by the highest rate to be tested, was placed in a 20 mL glass vial and was dissolved in 4 mL of a 97:3 v/v (volume/volume) mixture of acetone and dimethyl sulfoxide to obtain concentrated stock solutions. If the test compound did not dissolve readily, the mixture was warmed and/or sonicated. The concentrated stock solutions obtained were diluted with an aqueous mixture containing acetone, water, iso-propyl alcohol, dimethyl sulfoxide, Atplus 411F crop oil concentrate, and Triton X-155 surfactant (methylenebisdiamyl phenoxy polyethoxy ethanol) in a 48.5:39:10:1.5:1.0:0.02 v/v ratio to obtain spray solutions of known concentration. The solutions containing the highest concentration to be tested were prepared by diluting 2 mL aliquots of the stock solution with 13 mL of the mixture and lower concentrations were prepared by dilution of appropriate smaller portions of the stock solution. Approximately 1.5 mL aliquots of each solution of known concentration were sprayed evenly onto each of the test plant pots using a Devilbiss atomizer driven by compressed air pressure of 2 to 4 psi (140 to 280 kiloPascals) to obtain thorough coverage of each plant. Control plants were sprayed in the same manner with the aqueous mixture. In this test an application rate of 1 ppm results in the application of approximately 1 g/ha.

The treated plants and control plants were placed in a greenhouse as described above and watered by sub-irrigation to prevent wash-off of the test compounds. After 2 weeks the condition of the test plants as compared with that of the untreated plants was determined visually and scored on a scale of 0 to 100 percent where 0 corresponds to no injury and 100 corresponds to complete kill. Some of the compounds tested, application rates employed, plant species tested, and results are given in Table 2.

TABLE 2

POSTEMERGENCE HERBICIDAL ACTIVITY

| Cpd. No. | Rate, ppm | STEME | XANST | CHEAL | IPOHE | AMARE | ABUTH | VIOTR | POLCO | ALOMY | SETFA | SORBI | AVEFA |
|---|---|---|---|---|---|---|---|---|---|---|---|---|---|
| 1 | 7.8 | 95 | 85 | 90 | 80 | 90 | 85 | 75 | 95 | 90 | 98 | 90 | 95 |
| 2 | 15.6 | 98 | 70 | 90 | — | 95 | 95 | 90 | 98 | 98 | 98 | 100 | 98 |
| 3 | 3.9 | 95 | 75 | 95 | — | 98 | 80 | 90 | 98 | 95 | 98 | 70 | 70 |
| 4 | 3.9 | 99 | 70 | 95 | 90 | 100 | 95 | 90 | 95 | 95 | 100 | 95 | 98 |
| 5 | 62.5 | 98 | 100 | 95 | 80 | 100 | 98 | 90 | 98 | 95 | 98 | 100 | 99 |
| 6 | 31.3 | 98 | 95 | 95 | 70 | 100 | 95 | 90 | 98 | 90 | 95 | 95 | 95 |

TABLE 2-continued

POSTEMERGENCE HERBICIDAL ACTIVITY

| Cpd. No. | Rate, ppm | STEME | XANST | CHEAL | IPOHE | AMARE | ABUTH | VIOTR | POLCO | ALOMY | SETFA | SORBI | AVEFA |
|---|---|---|---|---|---|---|---|---|---|---|---|---|---|
| 7 | 62.5 | 90 | 40 | — | 80 | 95 | 70 | 80 | 85 | 95 | 95 | 80 | 90 |
| 8 | 31.3 | 98 | 100 | — | 95 | 100 | 100 | 85 | 98 | 80 | 100 | 80 | 60 |
| 9 | 62.5 | 50 | 70 | 80 | 10 | 70 | 30 | 50 | 50 | — | 30 | 30 | 20 |
| 10 | 7.8 | 85 | 50 | 95 | 20 | 95 | 50 | 85 | 85 | 80 | 80 | 85 | 90 |
| 11 | 62.5 | 95 | 100 | 100 | 80 | 100 | 100 | 90 | 100 | 60 | 100 | 50 | 30 |
| 12 | 62.5 | 90 | 100 | 100 | 98 | 100 | 98 | 100 | 98 | 60 | 98 | 90 | 70 |
| 13 | 31.3 | 85 | 90 | 70 | 70 | 95 | 70 | 80 | 80 | 85 | 90 | 90 | 75 |
| 14 | 7.8 | 98 | 100 | 100 | 80 | 100 | 90 | 90 | 90 | 70 | 90 | 70 | 50 |
| 15 | 7.8 | 98 | 90 | 95 | — | 98 | 95 | 95 | 98 | 99 | 100 | 98 | 98 |
| 16 | 125 | 60 | 0 | 40 | 20 | 75 | 10 | 50 | 20 | 60 | 75 | 50 | 50 |
| 17 | 15.6 | 75 | 90 | 100 | 70 | 100 | 78 | 98 | 75 | 90 | 90 | 90 | 90 |
| 18 | 31.3 | 100 | 85 | 95 | 70 | 100 | 90 | 80 | 60 | 65 | 85 | 90 | 50 |
| 19 | 15.6 | 95 | 90 | 95 | 75 | 90 | 75 | 90 | 90 | 80 | 60 | 50 | 50 |

STEME = chickweed (*Stellaria media*)
CHEAL = lambsquarters (*Chenopodium album*)
AMARE = pigweed (*Amaranthus retroflexus*)
VIOTR = viola (*Viola tricolor*)
ALOMY = blackgrass (*Alopecurus myosuroides*)
SORBI = Rox orange sorghum (*Sorghum bicolor*)
XANST = cocklebur (*Xanthium strumarium*)
IPOHE = morningglory (*Ipomoea hederacea*)
ABUTH = velvetleaf (*Abutilion theophrasti*)
POLCO = wild buckwheat (*Polygonum convolvulus*)
SEFTA = giant foxtail (*Setaria faberi*)
AVEFA = wild oats (*Avena fatua*)

6. Evaluation of Preemergence Herbicidal Activity

Seeds of the desired test plant species were planted in a soil matrix prepared by mixing a loam soil which was composed of about 43 percent silt, 19 percent clay, and 38 percent sand and had a pH of about 8.1 and an organic matter content of about 1.5 percent and sand in a 70 to 30 ratio. The soil matrix was contained in plastic pots with a surface area of 161 square centimeters. When required to ensure good germination and healthy plants, a fungicide treatment and/or other chemical or physical treatment was applied.

A weighed amount, determined by the highest rate to be tested, of each test compound was placed in a 20 mL glass vial and was dissolved in 8 mL of a 97:3 v/v (volume/volume) mixture of acetone and dimethyl sulfoxide to obtain concentrated stock solutions. If the test compound did not dissolve readily, the mixture was warmed and/or sonicated. The stock solutions obtained were diluted with a 99.9:0.1 mixture of water and Tween® 155 surfactant (ethoxylated sorbitan fatty acid ester) to obtain application solutions of known concentration. The solutions containing the highest concentration to be tested were prepared by diluting 4 mL aliquots of the stock solution with 8.5 mL of the mixture and lower concentrations were prepared by dilution of appropriate smaller portions of the stock solution. A 2.5 mL aliquot of each solution of known concentration was sprayed evenly onto the soil of each seeded pot using a Cornwall 5.0 mL glass syringe fitted with a TeeJet TN-3 hollow cone nozzle to obtain thorough coverage of the soil in each pot. Control pots were sprayed in the same manner with the aqueous mixture. A highest application rate of 4.48 kg/ha is achieved when 50 mg of test compound is employed.

The treated pots and control pots were placed in a greenhouse with an approximately 15 hr photoperiod which was maintained at about 23–29° C. during the day and 22–28° C. during the night. Nutrients and water were added on a regular basis and supplemental lighting was provided with overhead metal halide 1000 Watt lamps as necessary. The water was added by top-irrigation. After 3 weeks the condition of the test plants that germinated and grew as compared with that of the untreated plants that germinated and grew was determined visually and scored on a scale of 0 to 100 percent where 0 corresponds to no injury and 100 corresponds to complete kill or no germination. Some of the compounds tested, application rates employed, plant species tested, and results are given in Table 3.

TABLE 3

PREEMERGENCE HERBICIDAL ACTIVITY

| Cpd. No. | Rate, g/Ha | XANST | CHEAL | IPOHE | AMARE | ABUTH | EPHHL | ALOMY | ECHCG | DIGSA | SETFA | SORBI | AVEFA |
|---|---|---|---|---|---|---|---|---|---|---|---|---|---|
| 1 | 17.5 | 100 | 98 | 80 | 100 | 99 | 70 | 100 | 98 | 98 | 95 | 98 | 100 |
| 2 | 17.5 | 80 | — | 85 | 100 | 75 | 85 | 100 | 60 | 80 | 100 | 95 | 75 |
| 3 | 17.5 | 100 | — | 98 | 100 | 100 | 90 | 100 | 100 | 100 | 100 | 100 | 95 |
| 4 | 17.5 | 85 | — | 98 | 99 | 98 | 98 | 100 | 100 | 100 | 99 | 100 | 100 |
| 5 | 70 | 85 | — | 75 | 99 | 95 | 90 | 100 | 98 | 99 | 98 | 95 | 99 |
| 6 | 35 | 70 | — | 50 | 98 | 98 | 80 | 100 | 90 | 100 | 98 | 95 | 90 |
| 7 | 70 | 0 | — | 10 | 100 | 0 | 20 | 100 | 20 | 40 | 100 | 95 | 70 |
| 8 | 17.5 | 80 | 100 | 90 | 100 | 85 | 90 | 95 | 100 | 85 | 100 | 95 | 30 |
| 9 | 70 | 0 | 30 | 30 | 40 | 20 | 0 | 0 | 0 | 0 | 20 | 0 | 0 |

TABLE 3-continued

PREEMERGENCE HERBICIDAL ACTIVITY

| Cpd. No. | Rate, g/Ha | XANST | CHEAL | IPOHE | AMARE | ABUTH | EPHHL | ALOMY | ECHCG | DIGSA | SETFA | SORBI | AVEFA |
|---|---|---|---|---|---|---|---|---|---|---|---|---|---|
| 10 | 35 | — | 90 | 0 | 98 | 60 | 40 | 30 | 80 | 0 | 40 | 100 | 80 |
| 11 | 17.5 | 90 | 100 | 98 | 100 | 100 | 90 | 100 | 100 | 80 | 100 | 90 | 60 |
| 12 | 17.5 | 80 | 100 | 90 | 98 | 70 | 90 | 70 | 100 | 80 | 90 | 98 | 30 |
| 13 | 35 | 50 | 95 | 50 | 95 | 60 | 50 | 95 | 80 | 100 | 95 | 95 | 85 |
| 14 | 17.5 | 70 | 95 | 75 | 95 | 85 | 85 | 80 | 80 | 80 | 85 | 85 | 60 |
| 15 | 17.5 | 95 | 100 | 95 | 70 | 95 | 98 | 100 | 98 | 98 | 100 | 100 | 98 |
| 16 | 140 | 40 | 20 | 0 | 85 | 20 | 0 | 40 | 0 | 0 | 10 | 40 | 30 |
| 17 | 17.5 | 65 | 100 | 60 | 100 | 75 | 100 | 99 | 100 | 100 | 100 | 99 | 90 |
| 18 | 35 | 70 | 100 | 90 | 100 | 95 | 70 | 100 | 90 | 100 | 100 | 100 | 70 |
| 19 | 35 | 85 | 100 | 50 | 100 | 80 | 50 | 100 | 70 | 80 | 30 | 60 | 60 |

XANST = cocklebur (*Xanthium strumarium*)
IPOHE = morningglory (*Ipomoea hederacea*)
ABUTH = velvetleaf (*Abutilion theophrasti*)
ALOMY = blackgrass (*Alopecurus myosuroides*)
DIGSA = crabgrass (*Digitaria sanguinalis*)
SORBI = Rox orange sorghum (*Sorghum bicolor*)
CHEAL = lambsquarters (*Chenopodium album*)
AMARE = pigweed (*Amaranthus retroflexus*)
EPHHL = wild poinsettia (*Euphorbia heterophylla*)
ECHCG = barnyardgrass (*Echinochloa crus-galli*)
SETFA = giant foxtail (*Setaria faberi*)
AVEFA = wild oats (*Avena fatua*)

7. Evaluation of Postemergence Herbicidal Activity with Safener

Pre-formulated test materials utilized were as follows: Compound 15 as a 30 g ai/L emulsified concentrate (3% Compound 15, 3% Agrimer AL-10 (copolymer of 1-ethenyl-2-pyrolidinone and 1-butene), 94% N-methyl pyrrolidone w/w) and cloquintocet-mexyl (CQC) as a 120 g ai/L emulsified concentrate (12% cloquintocet-mexyl, 2.5% Toximul D, 2.5% Toximul H, [blends of calcium dodecylbenzenesulfonate plus castor oil ehtoxylates, nonylphenol ethoxylates and EO-PO block copolymers] 83% aromatic 200 w/w). Diluted stock solutions of formulated materials were made in distilled water. Final spray solutions were made by adding specified aliquots of diluted stock materials to a solution containing distilled water and X-77 surfactant at 0.25% v/v. The solutions were applied using a mechanized track-sprayer calibrated to deliver 187 l/ha carrier volume with a nozzle (flat fan) pressure of 276 kilopascals.

Assessment of weed control and crop injury was taken a 3 weeks after application. Plant injury was visually assessed on a scale of 0 to 100% with 0 equal to no injury and 100 equal to complete kill. One of the compounds tested, application rates employed, plant species tested, and results are given in Table 4.

TABLE 4

Postemergence herbicidal data with and without safeners.

| Cpd. No. | Rate (g/ha) | % Injury TRZAS | % Control 3 Weeks After Application | | | | |
|---|---|---|---|---|---|---|---|
| | | | AVEFA | LOLMU | ALOMY | APSEV | SETVI |
| 15 | 25 | 47 | 99 | 99 | 99 | 100 | 99 |
| 15 + CQC (1:1) | 25 | 5 | 92 | 95 | 95 | 100 | 98 |
| 15 + CQC (1:5) | 25 | 0 | 90 | 92 | 94 | 97 | 99 |

| Code | Scientific Name | Common Name |
|---|---|---|
| TRZAS | *Triticum aestivum* | Spring wheat |
| AVEFA | *Avena fatua* | Wild oat |
| LOLMU | *Lolium multiflorum* | Italian ryegrass |
| ALOMY | *Alopecurus myosuroides* | Blackgrass |
| APSEV | *Apera spica-venta* | Windgrass |
| SETVI | *Setaria viridis* | Green foxtail |

What is claimed is:

1. An N-(5,7-dimethoxy[1,2,4]triazolo[1,5-a]pyrimidin-2-yl)arylsulfonamide compound of Formula I:

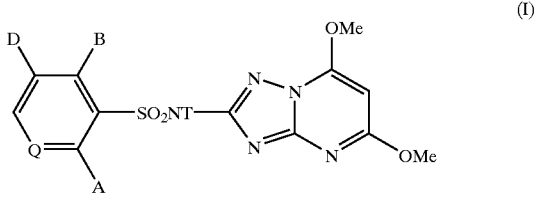

wherein

Q represents N or C—H;

A and B independently represent H, halo, R, OR' or $CO_2R''$ with the proviso that A and B are not both H;

D represents H, halo, or R;

T represents H, $SO_2R''$, C(O)R", C(O)OR", C(O)NR"$_2$, or $CH_2CH_2C(O)OR''$;

R represents $C_1$–$C_3$ alkyl each optionally possessing up to the maximum possible number of fluoro substituents;

R' represents $C_1$–$C_4$ alkyl, $C_3$–$C_4$ alkenyl, or $C_3$–$C_4$ alkynyl each optionally possessing up to the maximum possible number of fluoro substituents; and R" represents H or $C_{1-4}$ alkyl and, when T represents H, the agriculturally acceptable salts thereof.

2. A compound of claim 1 in which T represents H or an agriculturally acceptable salt thereof.

3. A compound of claim 2 in which Q represents CH.

4. A compound of claim 3 in which one of A or B represents $OCH_3$, the other of A or B represents halo, R, OR' or $CO_2R''$, and D represents H.

5. A compound of claim 3 in which A represents $OCH_3$, B represents H, and D represents H, $CH_3$ or Cl.

6. A compound of claim 3 in which A represents halo, R, OR', or $CO_2R''$, B represents $CF_3$, and D represents H.

7. A compound of claim 2 in which Q represents N.

8. A compound of claim 7 in which one of A or B represents $OCH_3$, the other of A or B represents halo, R, OR' or $CO_2R''$, and D represents H.

9. A compound of claim 7 in which A represents $OCH_3$, B represents H, and D represents H, $CH_3$ or Cl.

10. A compound of claim 7 in which A represents halo, R, OR', or $CO_2R''$, B represents $CF_3$, and D represents H.

11. A composition comprising an herbicidal amount of an N-(5,7-dimethoxy[1,2,4]triazolo[1,5-a]pyrimidin-2-yl)arylsulfonamide compound of Formula I:

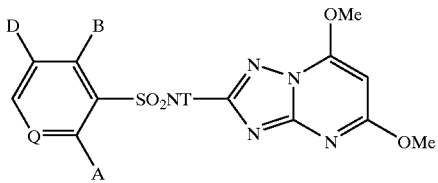

(I)

wherein

Q represents N or C—H;

A and B independently represent H, halo, R, OR' or $CO_2R''$ with the proviso that A and B are not both H;

D represents H, halo, or R;

T represents H, $SO_2R''$, C(O)R", C(O)OR", C(O)NR"$_2$, or $CH_2CH_2C(O)OR''$;

R represents $C_{1-3}$ alkyl each optionally possessing up to the maximum possible number of fluoro substituents;

R' represents $C_1$–$C_4$ alkyl, $C_3$–$C_4$ alkenyl, or $C_3$–$C_4$ alkynyl each optionally possessing up to the maximum possible number of fluoro substituents; and R" represents H or $C_1$–$C_4$ alkyl and, when T represents H, the agriculturally acceptable salts thereof in admixture with an agriculturally acceptable adjuvant or carrier.

12. A composition of claim 11 in which T represents H or an agriculturally acceptable salt thereof.

13. A composition of claim 12 in which Q represents CH.

14. A composition of claim 13 in which one of A or B represents $OCH_3$, the other of A or B represents halo, R, OR' or $CO_2R''$, and D represents H.

15. A composition of claim 13 in which A represents $OCH_3$, B represents H, and D represents H. $CH_3$ or Cl.

16. A composition of claim 13 in which A represents halo, R, OR', or $CO_2R''$, B represents $CF_3$, and D represents H.

17. A composition of claim 12 in which Q represents N.

18. A composition of claim 17 in which one of A or B represents $OCH_3$, the other of A or B represents halo, R, OR' or $CO_2R''$, and D represents H.

19. A composition of claim 17 in which A represents $OCH_3$, B represents H, and D represents H, $CH_3$ or Cl.

20. A composition of claim 17 in which A represents halo, R, OR', or $CO_2R''$, B represents $CF_3$, and D represents H.

21. A method of controlling undesirable vegetation which comprises applying to the vegetation or to the locus thereof an herbicidally effective amount of an N-(5,7-dimethoxy[1,2,4]triazolo[1,5-a]pyrimidin-2-yl)arylsulfonamide compound of Formula I:

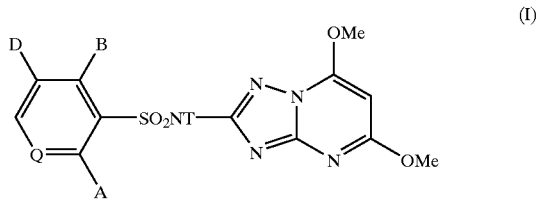

(I)

wherein

Q represents N or C—H;

A and B independently represent H, halo, R, OR' or $CO_2R''$ with the proviso that A and B are not both H;

D represents H, halo, or R;

T represents H, $SO_2R''$, C(O)R", C(O)OR", C(O)NR"$_2$, or $CH_2CH_2C(O) OR''$;

R represents $C_{1-3}$ alkyl each optionally possessing up to the maximum possible number of fluoro substituents;

R' represents $C_1$–$C_4$ alkyl, $C_3$–$C_4$ alkenyl, or $C_3$–$C_4$ alkynyl each optionally possessing up to the maximum possible number of fluoro substituents; and R" represents H or $C_1$–$C_4$ alkyl and, when T represents H, the agriculturally acceptable salts thereof.

22. A method of claim 21 in which T represents H or an agriculturally acceptable salt thereof.

23. A method of claim 22 in which Q represents CH.

24. A method of claim 23 in which one of A or B represents $OCH_3$, the other of A or B represents halo, R, OR' or $CO_2R''$, and D represents H.

25. A method of claim 23 in which A represents $OCH_3$, B represents H, and D represents H, $CH_3$ or Cl.

26. A method of claim 23 in which A represents halo, R, OR', or $CO_2R''$, B represents $CF_3$, and D represents H.

27. A method of claim 22 in which Q represents N.

28. A method of claim 27 in which one of A or B represents $OCH_3$, the other of A or B represents halo, R, OR' or $CO_2R''$, and D represents H.

29. A method of claim 27 in which A represents $OCH_3$, B represents H, and D represents H, $CH_3$ or Cl.

30. A method of claim 27 in which A represents halo, R, OR', or $CO_2R''$, B represents $CF_3$, and D represents H.

31. A process for the preparation of an N-(5,7-dimethoxy[1,2,4]triazolo[1,5-a]pyrimidin-2-yl)arylsulfonamide compound of Formula I:

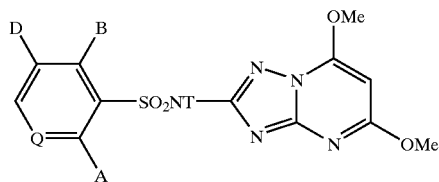
(I)

wherein

Q represents N or C—H;

A and B independently represent H, halo, R, OR' or $CO_2R''$ with the proviso that A and B are not both H;

D represents H, halo, or R;

T represents H, $SO_2R''$, $C(O)R''$, $C(O)OR''$, $C(O)NR''_2$, or $CH_2CH_2C(O)OR''$;

R represents $C_1-C_3$ alkyl each optionally possessing up to the maximum possible number of fluoro substituents;

R' represents $C_1-C_4$ alkyl, $C_3-C_4$ alkenyl, or $C_3-C_4$ alkynyl each optionally possessing up to the maximum possible number of fluoro substituents; and R" represents H or $C_1-C_4$ alkyl which comprises combining a compound of the formula (II):

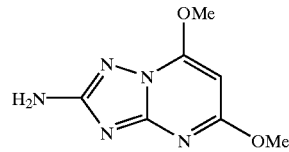
(II)

with a arylsulfonyl chloride compound of Formula III:

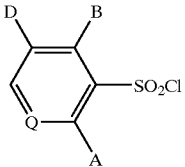
(III)

wherein

A, B, D, and Q are as defined for compounds of Formula I in a polar, aprotic solvent under anhydrous conditions and adding pyridine as a base and a catalytic amount of dimethyl sulfoxide.

* * * * *

UNITED STATES PATENT AND TRADEMARK OFFICE
CERTIFICATE OF CORRECTION

PATENT NO.   : 6,559,101 B2
DATED        : May 6, 2003
INVENTOR(S)  : Timothy C. Johnson et al.

It is certified that error appears in the above-identified patent and that said Letters Patent is hereby corrected as shown below:

<u>Title page, Item [54] and Column 1, lines 1 thru 4,</u>
Title, should read
-- N-(5,7-DIMETHOXY[1,2,4]TRIAZOLO[1,5-a]PYRIMDIN-2-YL) ARYLSULFONAMIDE COMPOUNDS AND THEIR USE AS HERBICIDES --

<u>Column 2,</u>
Line 6, should read
-- R' represents $C_1$-$C_4$ alkyl, $C_3$-$C_4$ alkenyl, or $C_3$-$C_4$ --

<u>Column 17,</u>
Line 13, should read
-- R" represents H or $C_1$-$C_4$ alkyl and, when T represents H, --
Line 53, should read
-- R represents $C_1$-$C_3$ alkyl each optionally possessing up to --

<u>Column 18,</u>
Line 41, should read
-- R represents $C_1$-$C_3$ alkyl each optionally possessing up to --

Signed and Sealed this

Second Day of September, 2003

JAMES E. ROGAN
*Director of the United States Patent and Trademark Office*